(12) United States Patent
Gilhuly et al.

(10) Patent No.: US 6,210,323 B1
(45) Date of Patent: Apr. 3, 2001

(54) SURGICAL ARM AND TISSUE STABILIZER

(75) Inventors: Terence J. Gilhuly; Septimiu E. Salcudean; Samuel V. Lichenstein; Kassem A. Ashe; Simon F. Bachmann, all of Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 09/310,138

(22) Filed: May 12, 1999

Related U.S. Application Data

(60) Provisional application No. 60/085,523, filed on May 5, 1998, and provisional application No. 60/089,014, filed on Jun. 12, 1998.

(51) Int. Cl.[7] .................................................. A61B 17/02
(52) U.S. Cl. ........................................ 600/210; 600/208
(58) Field of Search ................................. 600/228, 229, 600/210, 208, 212, 235, 201

(56) References Cited

U.S. PATENT DOCUMENTS

| | | | |
|---|---|---|---|
| 1,054,488 | * 2/1913 | Bailey | 600/229 |
| 1,382,783 | * 6/1921 | Howard | 600/229 |
| 1,440,401 | * 1/1923 | May | 600/228 |
| 1,460,697 | * 7/1923 | Bendlin | 600/229 |
| 3,278,207 | * 10/1966 | Barish et al. | 600/229 |
| 3,638,973 | * 2/1972 | Poletti | 600/229 |
| 3,858,578 | * 1/1975 | Milo | 600/229 |
| 4,143,652 | * 3/1979 | Meier et al. | 600/229 |
| 4,461,284 | * 7/1984 | Fackler | 600/228 |
| 5,609,565 | * 3/1997 | Nakamura | 600/229 |
| 5,865,730 | * 2/1999 | Fox et al. | 600/228 |

* cited by examiner

Primary Examiner—Paul J. Hirsch
(74) Attorney, Agent, or Firm—Oyen Wiggs Green & Mutala

(57) ABSTRACT

This invention is related to a novel passive medical device that can be used in surgery to stabilize tissue for anastomosis or other surgical work. More particularly, the tissue stabilization device and surgical arm stabilizes cardiac tissue which enables coronary artery bypass grafting surgeries to proceed while the heart is beating, or during other surgical procedures that require holding or retraction of tissue and arresting blood flow. A surgical arm comprising: (a) a first hollow link; (b) a second hollow link; (c) a hollow universal joint connecting an end of the first link with an end of the second link; (d) a support mount for the first link, the universal joint and the second link; and (e) a hollow tissue stabilizer connected to an end of a hollow link opposite to the hollow link that is proximate the support mount.

18 Claims, 7 Drawing Sheets

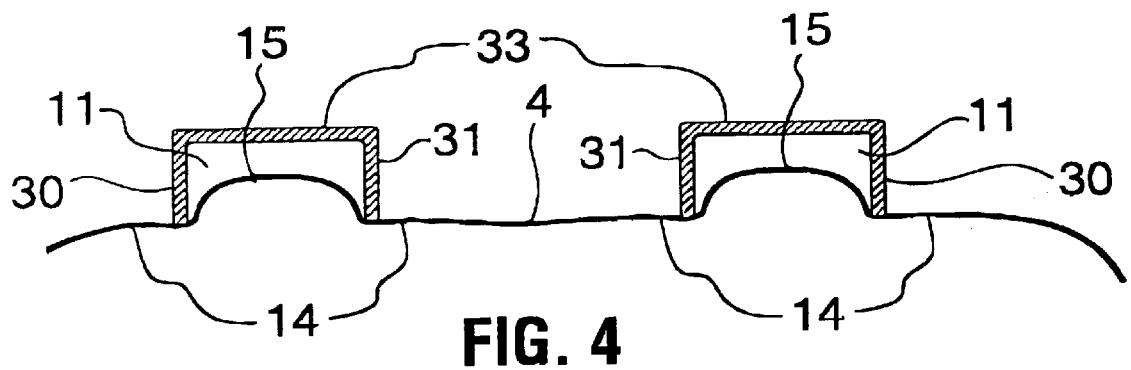
FIG. 4
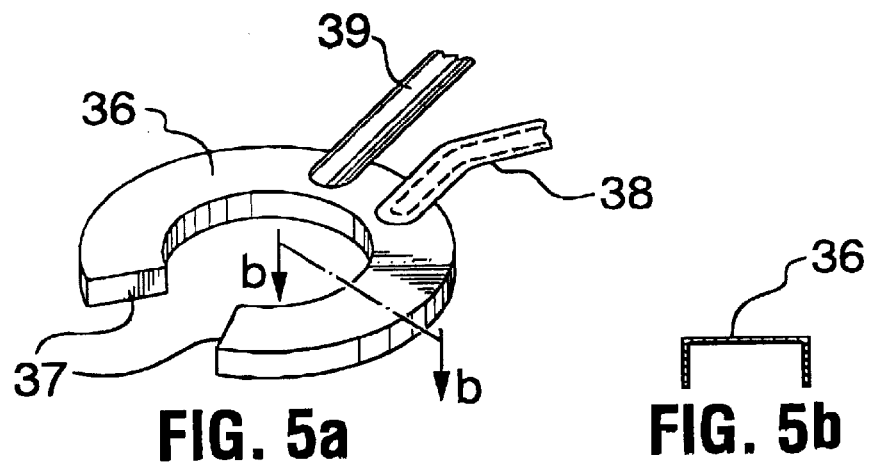
FIG. 5a
FIG. 5b
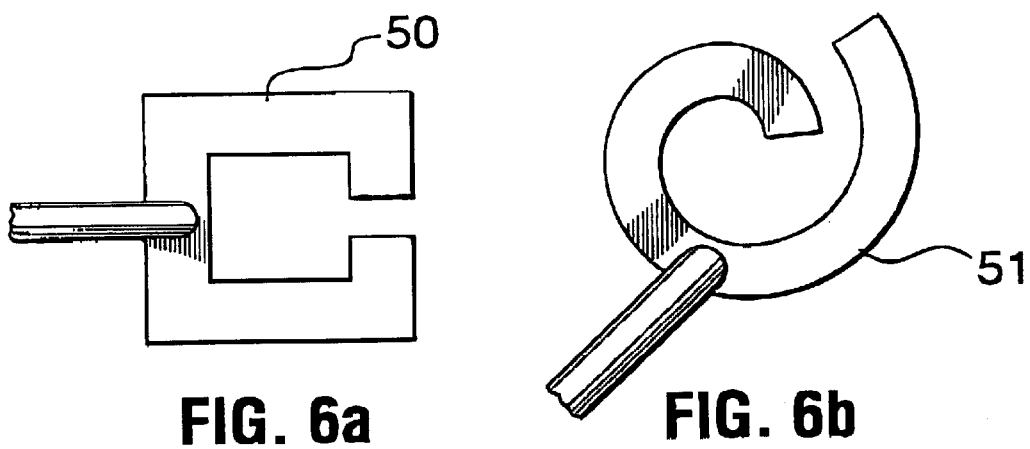
FIG. 6a
FIG. 6b

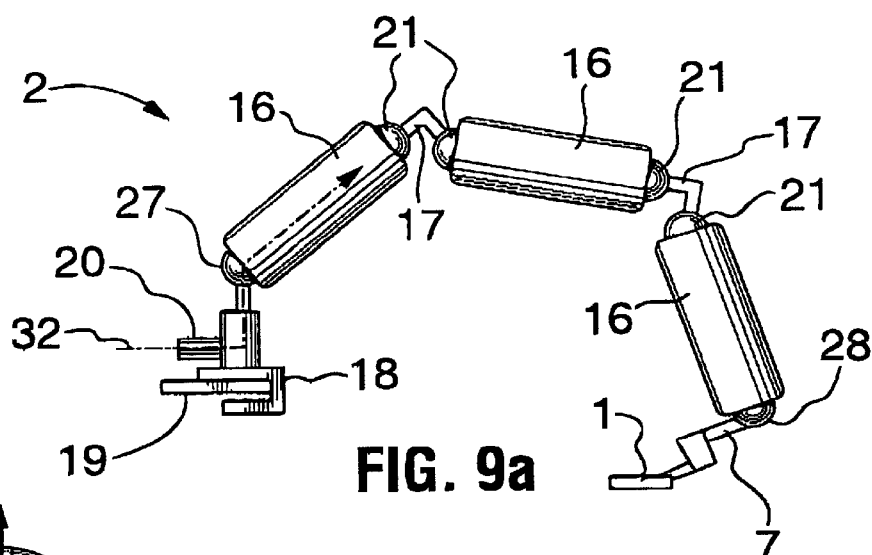
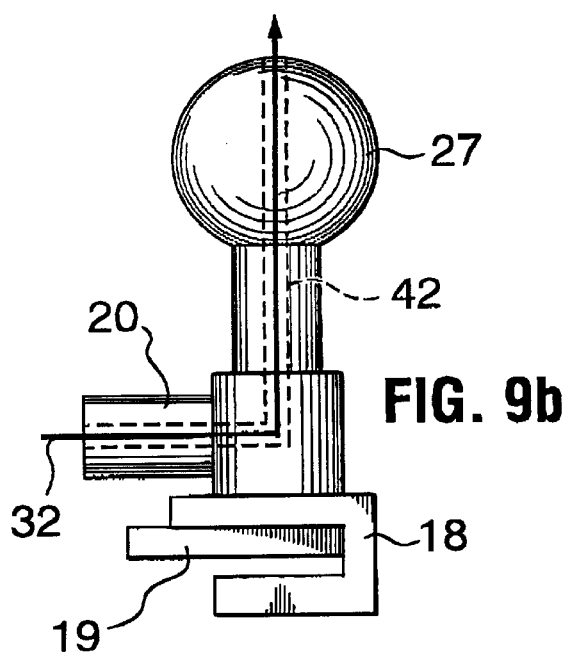
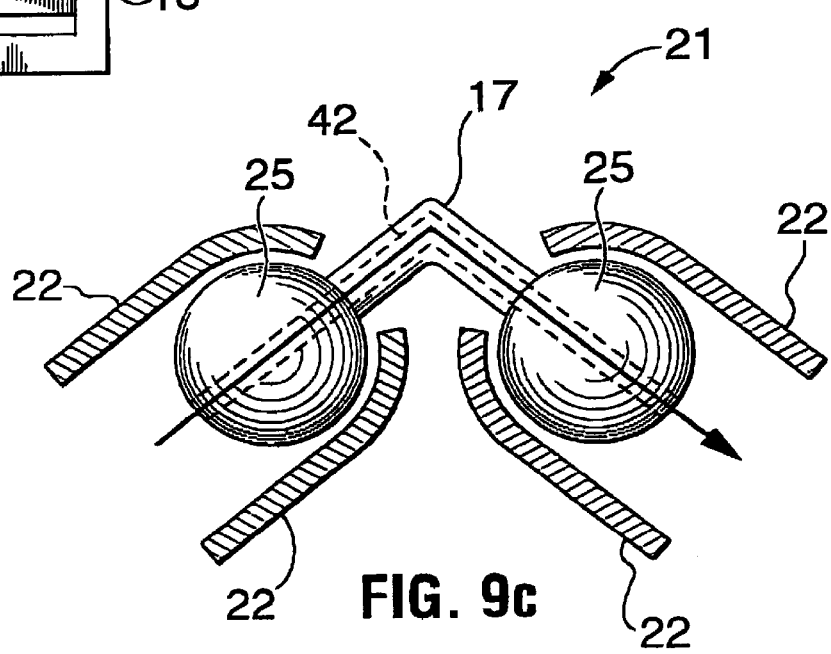
FIG. 9a
FIG. 9b
FIG. 9c

SURGICAL ARM AND TISSUE STABILIZER

This application claims the benefit of U.S. Provisional Application Ser. No. 60/085,523, filed May 5, 1998, and U.S. Provisional Application Ser. No. 60/089,014 filed Jun. 12, 1998.

FIELD OF THE INVENTION

This invention is related to a novel passive medical device that can be used in surgery to stabilize tissue for anastomosis or other surgical work.

More particularly, the tissue stabilization device and surgical arm stabilizes cardiac tissue which enables coronary artery bypass grafting surgeries to proceed while the heart is beating, or during other surgical procedures that require holding or retraction of tissue and arresting blood flow.

BACKGROUND OF THE INVENTION

Coronary artery bypass grafting surgeries are very challenging procedures that require suturing of tiny vessels (with diameters as small as 1.5 mm) on the surface of the heart. Presently the common practice is to stop the heart while such suturing takes place and bypass the natural blood oxygenation process through the lungs with an artificial cardiopulmonary bypass machine.

Because the disadvantages of cardio-pulmonary bypass are numerous and have been well documented in the literature (Kirkland, 1993; The Committee on Trauma, 1996), several approaches have been proposed to perform coronary artery bypass grafting surgery without stopping the heart. All such approaches require the stabilization of the cardiac tissue surrounding the coronary bypass site without significant bleeding to allow the above-mentioned delicate suturing to take place. Several approaches have been proposed to accomplish a stable operating field.

In one common approach, tissue surrounding the coronary is sutured to a fixed support, allowing the grafting surgery to proceed. The fixation suturing is time consuming and relies on significant tissue stretching to achieve a reasonably stable surgical field. Significant tissue motion is still present, implying that the quality of the grafts is not as high as it could be.

In another common approach, cardiac tissue stabilizers that press down on the coronary artery bypass site have been proposed. CTS (Cremer et al., 1997; Boonstra et al., 1997) and Guidant (Guidant Corporation, 1997) Corporations make devices that rely on a horseshoe shaped mechanism to push down the region of the coronary artery requiring bypass, trapping the heart tissue at this location. The CTS horseshoe (Cremer et al., 1997; Boonstra et al., 1997) is attached to a vertical rod which is screw-tightened to a slide which is screwmounted to a custom made chest retractor. This gives it three degrees of freedom. The Guidant device's horseshoe is fixated to the chest retractor through a flexible cable clamp mechanism screw also tightened to the retractor. The push-down mechanisms developed have to press on the heart with sufficient force to still be in contact with the cardiac tissue when the heart is fully contracted.

Another approach proposed in Borst et al., 1996, consists of using discrete suction cups around the coronary bypass site to fixate tissue with respect to the retractor or an adjustable surgical stand. In one of the embodiments of this approach, several sets of discrete suction cups are held on rods mounted on cable clamps, resembling an "Octopus" latching on tissue surrounding the surgical sight. In turn, the cable clamps are screw-fastened to an adjustable surgical stand or fastened to a support attached to the operating table. The art taught in Borst, 1996, has led to a product marketed by Medtronic called the "Octopus" device (Medtronic, 1997).

U.S. Pat. No. 5,727,569, Benetti et al., Mar. 17, 1998, discloses devices and techniques which use a negative (suction) pressure or vacuum, applied through a surgical instrument, to fix the position of a portion of the surface of a beating heart so that a surgical procedure can be more easily performed. The devices apply a negative pressure at several points on the outer surface of the heart such that a portion of the heart is fixed in place by the suction imposed through the surgical instrument. Because the instrument fixes the position of the tissue, and because the instruments remain at a constant distance from the particular portion of the heart where the surgery is being performed, the device may also serve as a support or platform so that other surgical instruments or devices can be advantageously used at the site. In certain perferred embodiments, the devices described herein have structures to facilitate the use of additional surgical instruments such that the placement of negative pressure device permits the surgeon to advantageously manipulate the other instruments during surgery. The negative pressure is preferably imposed through a plurality of ports which may be disposed in a substantially planar surface of the instrument which contacts the cardiac tissue.

WO 98/37814, Takahashi, published Sep. 3, 1998, discloses an improved device to hold an anastomotic site of coronary artery for the bypass surgery; to provide said device wherein the coronary artery bypass operation can be quickly and accurately performed on the beating heart by firmly and atraumatically holding said anastomotic site motionless and bloodless. That is to say, the characteristic feature of the present invention is in that the coronary artery can be stably held motionless without need to forcedly compress the heart surface. This is accomplished with a circular flexible suction device which surrounds the target artery, and whose center is open to expose the anastomotic site. The device is suctioned to the heart surface by drawing off the air in the flexible circular channel, creating negative pressure.

U.S. Pat. No. 5,749,892, Vierra, May 12, 1998, discloses a system and method for performing less invasive surgical procedures within a body cavity. In a preferred embodiment, the invention provides a system and method for isolating a surgical site such as an anastomosis between an internal mammary artery and a coronary artery in a thoracoscopic coronary artery bypass grafting procedure. The system comprises a foot pivotally coupled to the distal end of a shaft by a linkage. The foot has first and second engaging portions with contact surfaces for engaging a tissue surface. The engaging portions are movable between an open position, where the contact surfaces are separated by a gap, and a collapsed position, where the foot is configured for delivery through the percutaneous penetration. An actuator, at the proximal end of the shaft, can be rotated to pivot the foot about a transverse axis to that the contact surfaces are oriented generally parallel to the surgical site to apply pressure to the tissue structure on both side of the surgical site.

A number of surgical arms have been developed in the past for holding, positioning and supporting patient limbs during operation (Auchinleck et al., 1992; McEwen et al., 1993; McEwen et al., 1993).

U.S. Pat. No. 4,616,632, Wigoda, Oct. 14, 1986, discloses a set of retractors which are coupled by releasable locks to rods on the side of an operating table. A foot pedal is provided to release the locks and allow the retractors to be repositioned easily and with one hand by the doctor while performing the surgery. The foot pedal may utilize hydraulic fluid to lock or release the movement of the retractors. The joint holding the retractors is also rendered free to rotate to properly position the retractors, when the foot pedal is depressed.

U.S. Pat. No. 4,863,133, Bonnell, Sep. 5, 1989, discloses an instrument-supporting, articulated device with a distal end capable of supporting an instrument in the region of a surgical operating site. The device has at least one joint that supports a movable distal support element relative to a proximal support, the joint being associated with a mode selector. The joint has structure capable, upon selection of a first mode of operation by the selector, of enabling relatively free motion of the joint for achieving a desired positon of the instrument and the joint has structure capable, upon selection of a second mode of operation by the selector, to set the position of the instrument in space with lightly loaded restraint. The lightly loaded restraint is of a value that, while the second mode continues to be selected, the user may adjust the position of the instrument by application of a light force to the instrument and upon release of such light force by the user, the instrument will remain in the newly adjusted position.

U.S. Pat. No. 5,201,325, McEwen et al., Apr. 13, 1993, discloses an apparatus useful in surgery for holding retractors and other surgical instrumentation in a number of different positions required by a surgeon for the performance of a surgical procedure, including advanced sensing and regulation of retraction pressures and position; and incorporating a force amplification method to drive a locking mechanism in the supporting structure that utilizes a constrained, substantially incompressible, flexible solid material to yield a mechanism that is suitable for clinical use.

The surgical arms designed for holding, positioning and supporting patient limbs during operation must handle very significant loads. For this purpose, these devices are endowed with pneumatic brakes that include mechanical force multiplication that makes their design and constructions quite complicated and expensive. Similar approaches used in the design of above pneumatic limb positioning and holding devices have been used in the design of a passive pneumatic camera holder, the Endex arm (Andronic Devices, 1994). The Endex arm uses a number of internally pressurized links and single axis pneumatic brakes to lock in position a camera holder at the site required by a laparoscopic surgeon. Computer Motion's AESOP (Automated Endoscopic System for Optimal Positioning) 3000 (Sackier, 1996) is an FDA-approved voice controlled active arm used for maneuvering and positioning an endoscopic camera for laparoscopy.

Another "general purpose" surgical holding arm that has been developed for holding endoscopic and orthopaedic tools is the "automatic, medical holding device" research arm described in Erbse et al., 1997. It is a passive arm with several links connected through ball joints at their ends. The ball joints are locked in place with piezoelectric actuators used as jams.

SUMMARY OF INVENTION

A novel system for the stabilization of cardiac tissue during off-pump (while the heart is still beating) coronary artery bypass grafting procedures is presented. This system brings together in a novel fashion a novel tissue holder that attaches to the heart and a novel surgical arm that immobilizes the tissue holder with respect to the patient's retractor or another reference frame. The tissue holder is a "C"-shaped hollow channel with a vacuum inlet. When the open section of the tissue holder is placed on a tissue and the vacuum is activated, the tissue is sucked within the channel resulting in holding forces. The tissue holder attaches to the distal end of a support arm. The proximal end of the support arm attaches to the patient's retractor, bed or other platform. The arm consists of several links attached to each other by ball joints that are locked in place by pneumatic pressure. It features a lightweight, quick to activate/deactivate, highly dextrous, unobtrusive design, with gas supplied to the links through piping interior to the arm.

The invention is directed to a surgical arm comprising: (a) a first hollow link; (b) a second hollow link; (c) a hollow universal joint connecting an end of the first link with an end of the second link; (d) a support mount for the first link, the universal joint and the second link; and (e) a hollow tissue stabilizer connected to an end of a hollow link opposite to the hollow link that is proximate the support mount.

The surgical arm can include a third hollow link, and a second hollow universal joint, located between the first hollow link, first hollow universal joint and second hollow link, to form three links in series, connected by hollow universal joints between the respective links.

The support mount can be a clamp which can be detachably affixed to a stable body. An end of the first hollow link, remote from the first hollow universal joint can be connected to the support mount by a hollow universal joint.

An end of the second hollow link, remote from the hollow universal joint, can be connected to the tissue stabilizer by a universal joint. The hollow universal joint can be biased to hold a position when the first hollow link is moved relative to the second hollow link.

The hollow universal joint can comprise a pair of joint balls connected together by a sleeve. The joint can include a groove and an O-ring in the groove to improve the seal. One part of the joint ball can be constructed of metal and the second part of the ball can constructed of a resilient material. The first ball and the second ball can be biased by a metal spring or by a spacer.

The universal joint can comprise a first ball and a second ball which can be housed in a tubular sleeve, which first and second balls can exert a force on the tubular channel when air pressure is applied to the interior of the tubular connector.

The tissue stabilizer can be constructed in the form of a hollow "C". The hollow "C"-shaped tissue stabilizer can have openings therein which can permit the tissue stabilizer to affix to tissue when a vacuum is applied to the interior of the "C"-shaped hollow tissue stabilizer. The surgical arm can include a suction machine which can draw a vacuum on the interior of the surgical arm and tissue stabilizer.

BRIEF DESCRIPTION OF DRAWINGS

In drawings which illustrate specific embodiments of the invention, but which should not be construed as restricting the spirit or scope of the invention in any way:

FIG. 4 illustrates an end section view of the cardiac tissue stabilizer with vacuum channel installed on tissue.

FIGS. 5a and 5b illustrate respectively a detailed perspective view of the cardiac tissue stabilizer with vacuum channel and suction hole, and a section view of the vacuum channel.

FIGS. 6a and 6b illustrate respectively alternative embodiments of the tissue stabilizer with vacuum channel.

FIGS. 9a, 9b and 9c illustrate respectively an elevation view and detail views of the assembled surgical arm and tissue stabilizer, arm mount and joint construction.

DETAILED DESCRIPTION OF SPECIFIC EMBODIMENTS OF THE INVENTION

Detailed Description of the Invention in Relation to the Drawings

Figure 1:
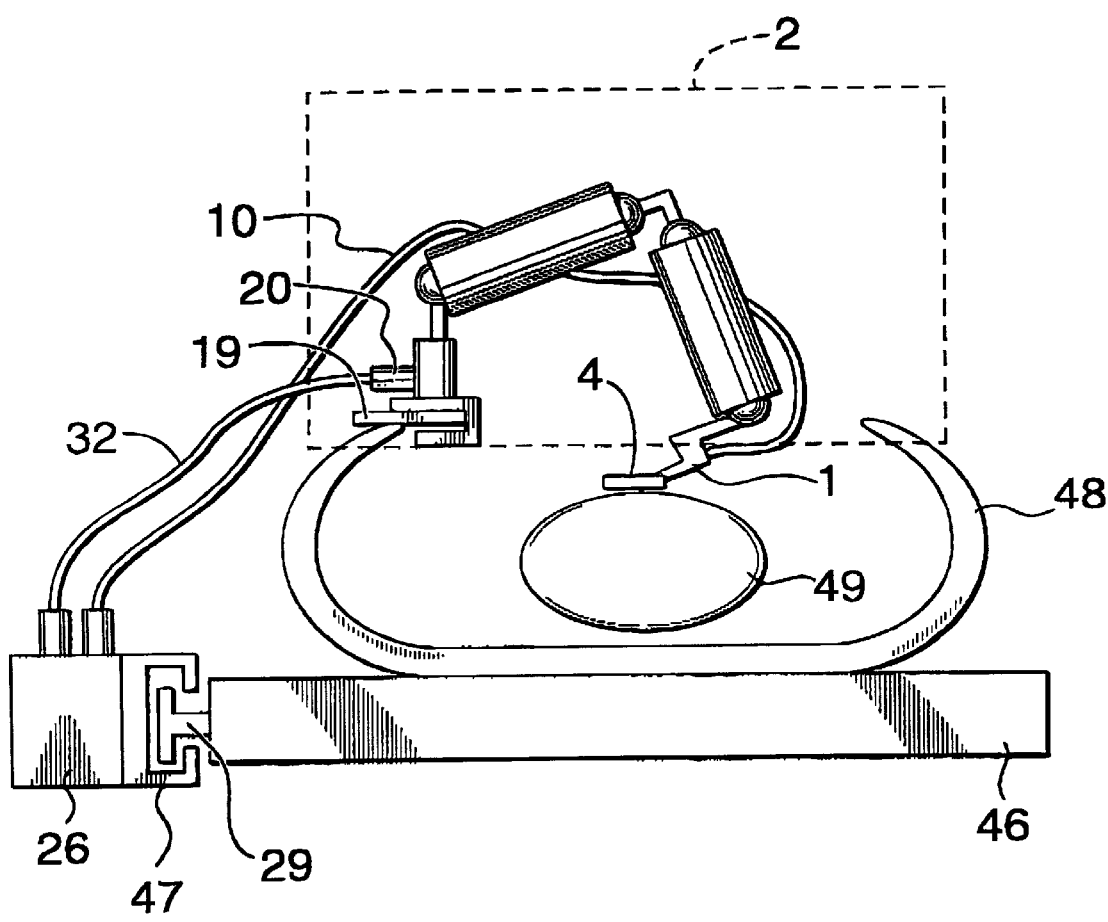
FIG. 1 illustrates a schematic end partial section view of the cardiac tissue stabilizer and surgical arm positioned on the heart of a patient.

FIG. 1 illustrates a schematic end partial section view of the cardiac tissue stabilizer and surgical arm positioned on the heart of a patient. The cardiac tissue stabilizer according to the invention comprises two parts, as shown in FIG. 1: a tissue holder 1, attached to a surgical arm 2. The tissue holder 1 at the distal end of the surgical arm 2 attaches to the heart 49 inside the rib cage 48 and creates a stable suturing area 4. The proximal end of the surgical arm 2 attaches to the patient's chest retractor 19 or to a surgical stand affixed to the operating table 46 or on the operating room floor (not shown). FIG. 1 also illustrates the operating table 46, a side rail 29, a clamp 47, an airflow suction tube 10, airflow channel 26, and air pressure tube 32.

Figure 2A:
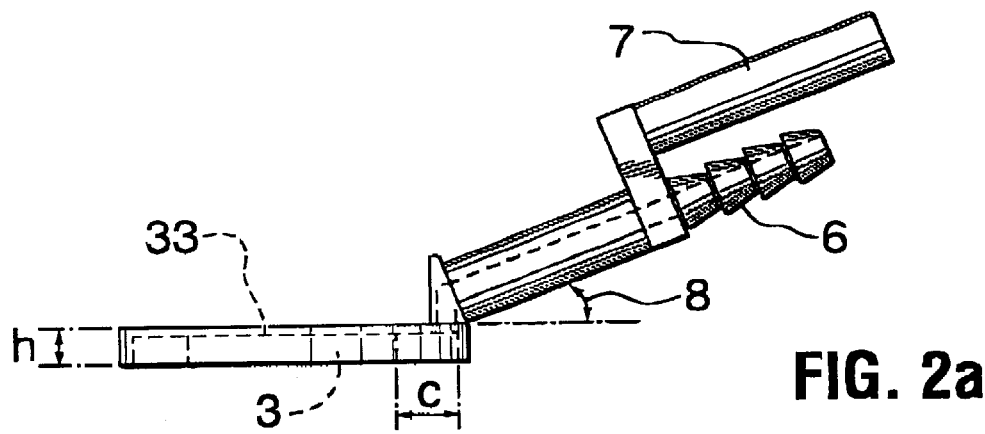
FIGS. 2a and 2b illustrate respectively elevation and plan views of the cardiac tissue stabilizer.
Figure 2B:
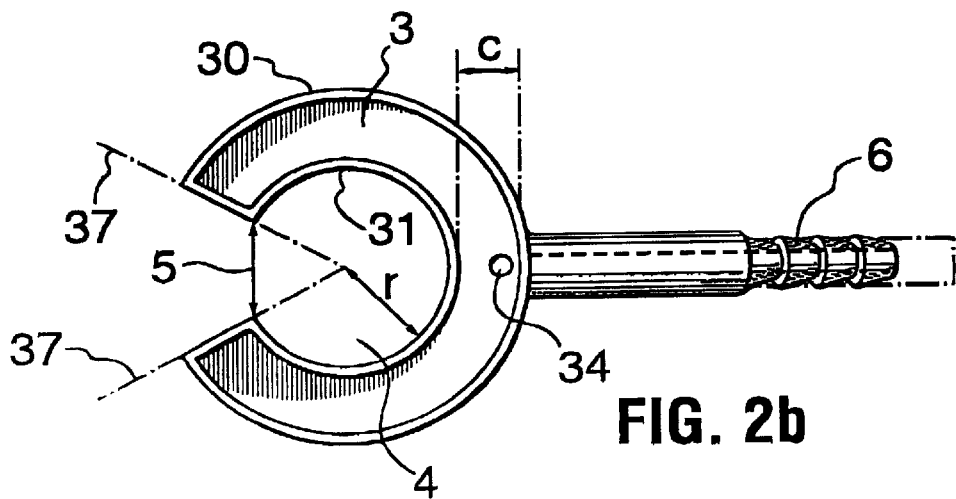
Figure 3:
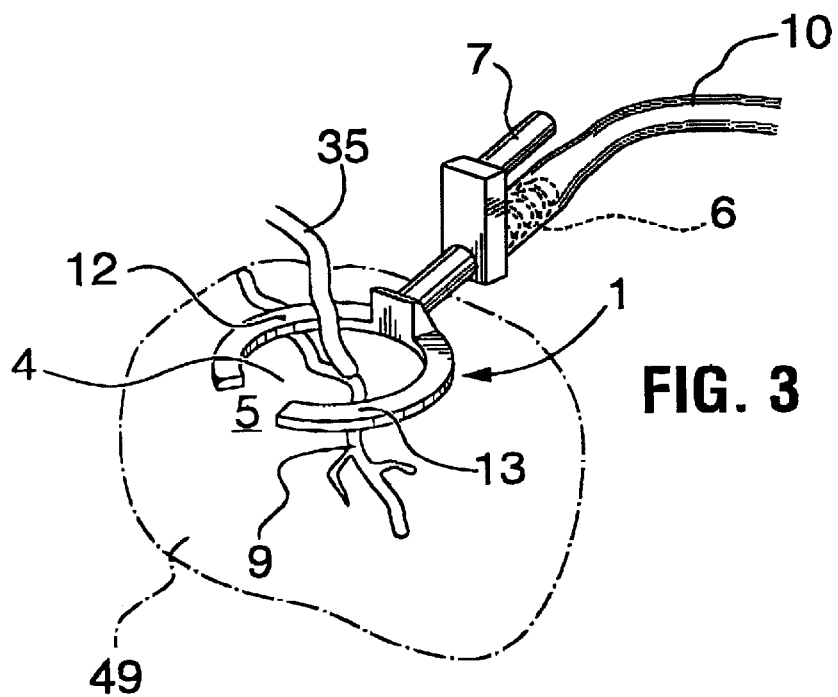
FIG. 3 illustrates an isometric view of the cardiac tissue stabilizer positioned on a heart.

FIGS. 2a and 2b illustrate respectively elevation and plan views of the cardiac tissue stabilizer. FIG. 3 illustrates an isometric view of the cardiac tissue stabilizer positioned on a heart. FIG. 4 illustrates an end section view of the cardiac tissue stabilizer with vacuum channel installed on tissue. FIGS. 2, 3 and 4 illustrate an embodiment of a C-shaped tissue holder 1 that uses vacuum suction to attach to the heart. The hollowed-out device illustrated in detail in FIGS. 2a and 2b consists of a vacuum channel 30, 31, 33 placed on the heart, a support member 7, and a vacuum port 6, as shown in FIG. 3. When vacuum is applied through tube 10, the heart tissue 14 is pulled inside the ring 30 as shown in the cross-section shown in FIG. 4 (tissue inhaled within the vacuum channel 15). A continuous vacuum volume is formed within the vacuum channel that is bounded by the heart tissue 14 on the underside of the C-section device and by the walls 30 of the device, namely the cylindrical section wall 30, the inner cylindrical section wall 31, the vacuum channel end walls 37 and the flat circular arc wall 33.

As shown in FIGS. 2a, 2b and 3, the vacuum suction for holding the tissue is delivered through the vacuum delivery hose port barb 6. This barb 6 is part of a support member 7 that connects the tissue holder 1 to the surgical arm 2. The support member 7 jogs to accommodate vacuum delivery hose barb 6 and is placed at hose barb angle 8 to the plane of application of tissue holder 1. This is done to allow easier application for the surgeons with less interference with the interior of the thoracic cavity.

The tissue holder 1, as seen particularly in FIGS. 2b and 3, is shaped as an open "C", rather than a closed "O"-ring to allow its removal following anastomosis of arterial grafts to the coronary artery 9 in surgical site 4. (An end-to-side anastomosis is shown in FIG. 3.) Once the grafting artery 35 is sutured to the coronary artery 9, the vacuum inside the C-shaped holder 1 can be switched off and the ring can be pulled free from the suture site in the direction of the support member 7. The sutured artery can pass through the gap 5.

In surgical application, as shown in FIG. 3, the tissue holder 1 is placed over a coronary artery 9. Vacuum pressure delivered by vacuum line 10 through hose barb 6 to vacuum port 34 (see FIG. 2b) creates a continuous vacuum surface 3 that pulls the heart tissue into vacuum volume 11 holding the tissue holder 1 to the heart and creating a flat unmoving surface 4 that the surgeon may suture to unimpeded by the beating of the heart. In addition, coronary artery 9 is inhaled at application points 12 and 13 (see FIG. 3) to temporarily cut off blood flow between application points 12 and 13, thus preventing blood from reducing vision in suturing site 4. In cross-section, this arrangement appears as in FIG. 4, where the inhaled cardiac tissue 15 is inhaled by the vacuum force in the C-shaped cross-section. Due to the compliance of cardiac tissue 14, 15 as it is pulled into vacuum volume 11, the heart tissue creates an effective compliant seal that is difficult to break.

It should be noted that, if necessary, there can be a manual or computer adjustment of vacuum pressure to allow the correct amount of tissue to be sucked into the ring 30. For example, the surgeon may be able to switch the vacuum on, but also adjust the vacuum level by proportionally turning a knob or pressing a pedal connected to the vacuum control. This allows the minimum vacuum level necessary for tissue stabilization to be used and could protect the cardiac tissue.

Experimentation with a number of vacuum holding devices (Gilhuly, 1998) has enabled the inventors to make the following observations (referring to FIG. 2):

(1) Vacuum holders with very small aspect ratio between the vertical walls height "h" and the horizontal wall cross-section "c" perform poorly as the heart tissue itself blocks the vacuum channel and reduces the holding force significantly.

(2) Vacuum holders that allow the heart tissue to be "inhaled" within their vacuum channel perform better, as the "inhaled" tissue creates an effective vacuum seal.

In order for the surgeon to work with the tissue stabilizer 1, the stabilized space 4 inside the "C" shape must be wide enough for suturing in and the height of the wall must not interfere with the surgeon's manipulation. An inner radius "r" of roughly 7 to 14 mm is preferred for the stabilized tissue area 4. A ratio of inner radius "r" to height "h" in the range of 5:3 has been found to work well in limiting the vacuum channel profile, thereby allowing the surgeon approximately 60 degrees of approach and suggesting an inner wall vacuum channel height "h" ranging between 4 and 8 mm.

Variations of the above vacuum tissue holder are possible within the spirit of the above described embodiment and the invention. An alternative design consisting of a vacuum channel 36 (with two vacuum channel ends 37), ported to a vacuum supply hose 38 and held by a rigid attachment, as shown in FIGS. 5a and 5b. The vacuum supply port and the rigid attachment, support post 39, can be one and the same part. Within the scope of the invention, there are many possible designs for the vacuum channel 36, as well as for the vacuum channel cross-section 409 also shown in section view in FIG. 5b.

Figure 7:
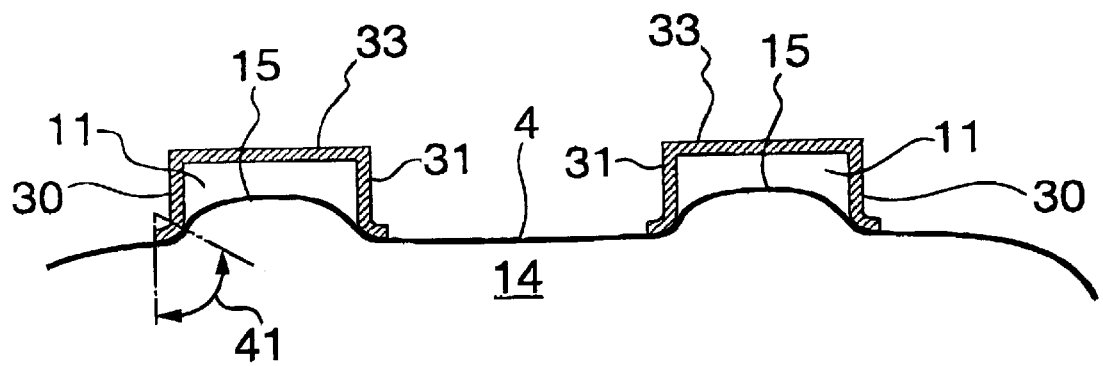
FIG. 7 illustrates an end section view of the cardiac tissue stabilizer vacuum channel installed on tissue, the vacuum channel having rounded bottom edges.
Figure 8A:
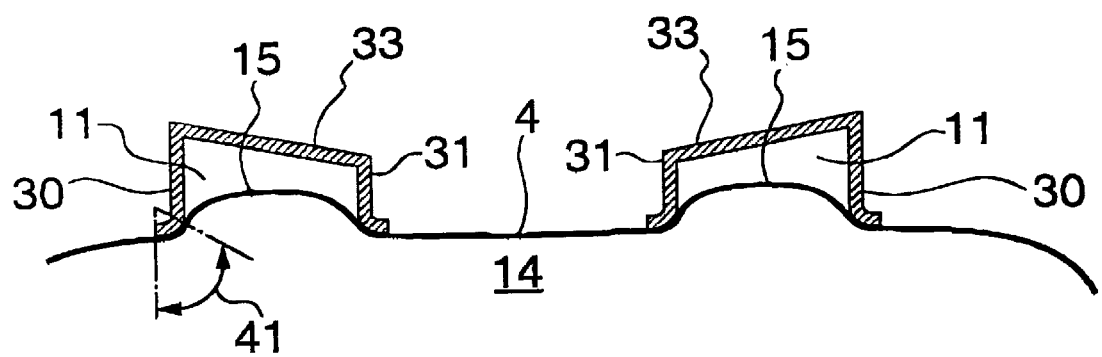
FIGS. 8a and 8b illustrate end section views of two alternative embodiments of the cardiac tissue stabilizer vacuum channel installed on tissue.
Figure 8B:
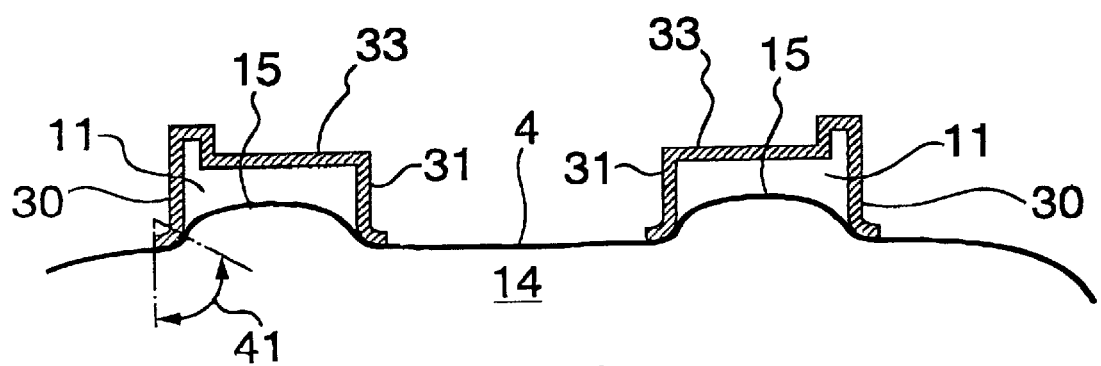

FIGS. 6a and 6b respectively show the design of a rectangular vacuum channel 50 and a spiral vacuum channel 51. In a further variation, the bottom edges of the vacuum channel cross-section can be curved outwardly as shown in FIG. 7, so as to make the heart tissue sealing surface area 41 larger. In further variants of the device, as shown in FIGS. 8a and 8b, the inner wall 31 of the tissue holder (vacuum channel) would be made shorter in height than the outer wall 30, thereby giving it the appearance of a stadium (FIG. 8a). The lower height inner wall 31 would provide reduced interference with the surgeons' work, thereby allowing them an approach to the surgical site 4 at a reduced angle.

Variations on this, including one with a small square vacuum channel added to and above the vacuum volume 11 adjacent to the outer wall 30 to approximate the stadium shape, as shown in FIG. 8b, are also possible.

To hold the tissue holder 1 fixated to the heart and form a rigid link between it and the patient or another reference frame, a multiple position surgical arm 2 is used. FIGS. 9a, 9b, 9c, 10 and 11 illustrate an embodiment of a surgical arm 2 that uses pressurized air to removably lock the tissue holder 1 to the patient retractor (see FIG. 1) or another reference frame.

In one embodiment as illustrated in FIGS. 9a, 9b, 9c, 10 and 11, 20 the surgical arm 2 consists of three hollow tubular links 16 having ball joints 21 at each of their adjacent ends. Each ball joint 21, as seen in FIG. 9c, has a ball 25 that can rotate inside and translate a small amount along the principal axis of a cylindrical sleeve 22. Each cylindrical sleeve 22 has a spherical end section matching the ball joint ball 25 to close radius tolerance. The amount of translation inside the cylindrical sleeve 22 is limited by a middle link segment 23 (see FIG. 10) that connects the sleeves 22 together and also acts as a spacer. The links 16 are connected to each other by connecting rods 17 that join adjacent ball joint balls 25. As seen in FIG. 9a, the first or proximal ball joint ball 27 of the surgical arm 2 is connected to the patient's retractor 19 or other reference by a base connector 18. The last or distal ball joint ball 28 of the surgical arm 2 is attached to the tissue holder 1 via the support member 7, as explained previously in relation to FIGS. 1, 2, 3 and 4.

As seen in the detail of FIGS. 9a, 9b, 9c and 10, each of the connecting rods 17 and the base connector 18, as well as the ball joint balls 25, 27, have therein hollowed-out gas delivery channels 42 that allow gas to flow from a pressurized gas delivery nozzle 20 in the base connector 18 to each and every link. The distal ball joint ball 28 does not have a channel in it.

Figure 11:
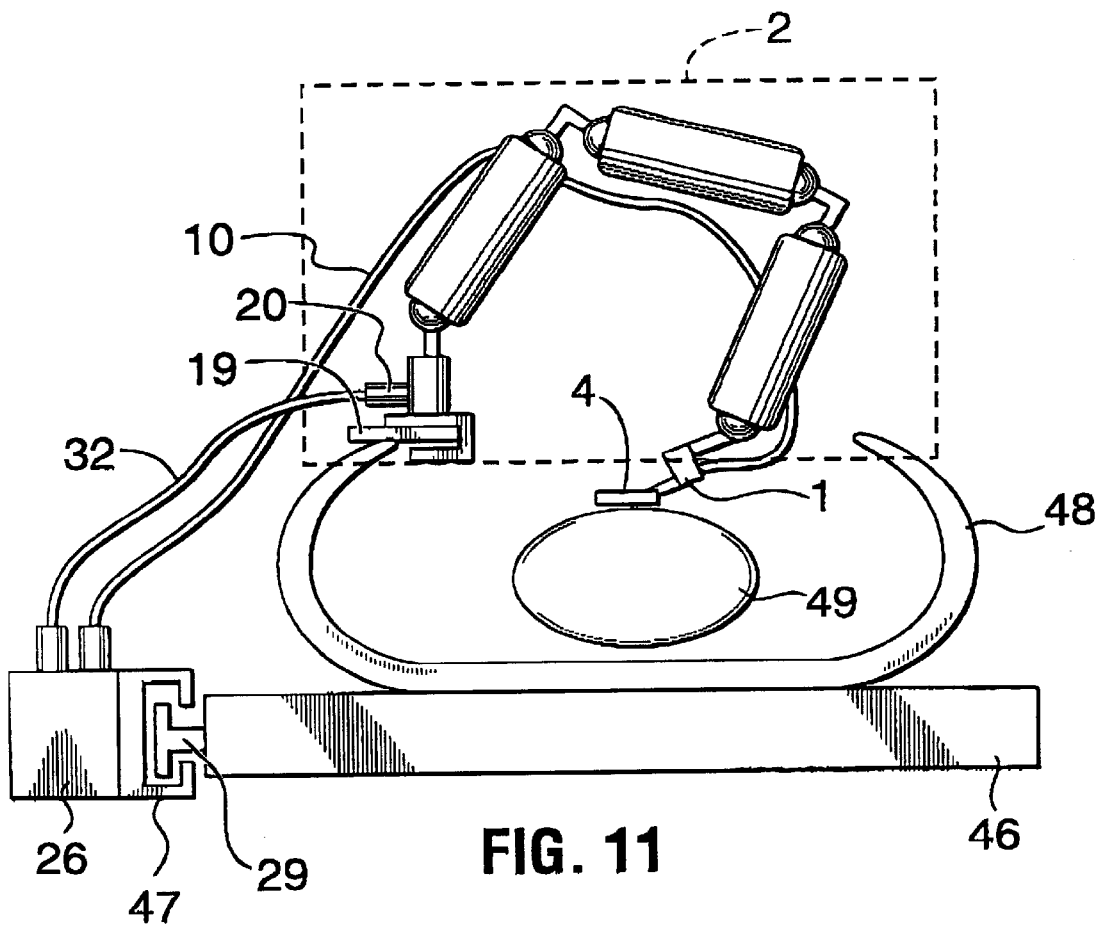
FIG. 11 illustrates a perspective view of one embodiment of the universal surgical arm and the C-shaped cardiac tissue stabilizer.

When the surgical arm 2 is not pressurized, each ball joint 21 allows three-degree-of-freedom angular motion of its connecting rod 17, base connector or distal support member through a limited pitch and roll and unlimited yaw angle, thereby giving the arm illustrated in FIGS. 9a and 11 eighteen degrees of freedom.

When the surgical arm 2 is pressurized through the gas delivery nozzle 20 by opening valves, air flows through the channel 26 (see FIG. 1) through pressure tube 1 the interior of the base connector 18, the proximal ball joint 27, the links 16 and the delivery channels 42 in the connecting rods 17 and through the ball joint balls 25. The pressurized gas then pushes each of the ball joint balls 25 against their matching spherical outer sleeve shells 22, with a force proportional to the gas pressure and the cross-sectional area of ball-outer-shell contact (this is close to the cylindrical cross-section 22). Friction forces developed between the ball joint balls 25 and the outer shells 22 lock the arm in its required configuration.

For a given tissue holder position and orientation (and implicit tissue holder support member 7 position and orientation), the arm redundancy allows the arm 2 to be locked in multiple (virtually an infinite number) configurations, some of which may be out of the surgeons' way and therefore advantageous. The connecting rods 17 may be angled at right angles as shown in FIGS. 9a and 9c, or at other angles or otherwise curved between the ball joint balls 25 in order to increase the dexterous reach of the arm 2 inside the thoracic cavity. Such bending removes some of the motion constraints imposed by the outer sleeve shells 22 which hold the ball joints 21 inside the links 16.

It will be understood that more or fewer links 16 interconnected by connecting rods 17 can be used in different implementations depending on the application and the surgeon's preference.

The links 16 and the connecting rods 17 can be made of stainless steel or any other high strength autoclavable material of accepted use in an operating room, with sealing materials such as urethane rubber or neoprene used to produce seals between the ball joint balls 25 and the links 16. The sleeves 22 and the middle link segments 23 are hermetically sealed, so once the ball joint balls 25 are pushed against the sleeves 22, pressurized air is trapped inside the surgical arm 2.

Figure 10:
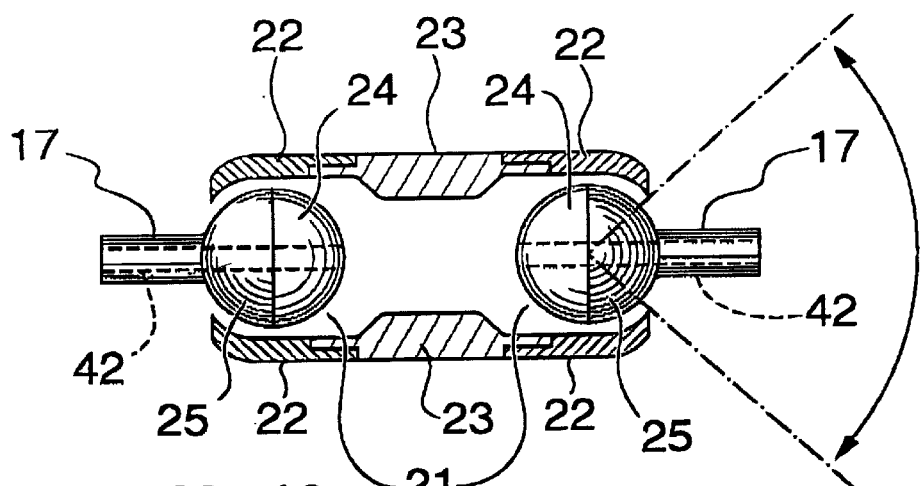
FIG. 10 illustrates a schematic section view of a hollow universal joint construction with two balls and a tube.

As an example of how sealing between the ball joint balls 25 and link sleeves 22 can be achieved, a particular embodiment is shown in FIG. 10. This embodiment uses ball joint balls made out of two adjoining hemispheres—a metal one 24 and a urethane rubber one 25. Contact between the ball joint balls and the link sleeves 22 is made through the urethane rubber material only, which has increased friction against stainless steel, would be the case if the ball was made of stainless steel or other hard metal. Furthermore, grooves can be cut, ground, etched or otherwise made in outer shell 22 to increase friction with the rubber hemisphere 25. The urethane rubber hemisphere 25 needs to be made from a durable, autoclavable rubber. It needs to be hard enough to prevent it from being extruded by the air pressure, yet compliant enough that it offers good friction contact. Both urethane rubber and neoprene have been found to be good materials for this purpose. It will be obvious to those skilled in the art that alternative designs do exist to increase friction in the pressurized ball joints presented above. The ball joint ball could be made out of steel or other hard material (potentially grooved), and the shell 22 can be made with an appropriate rubber gasket—an O-ring or a hemispherical gasket.

Figure 12:
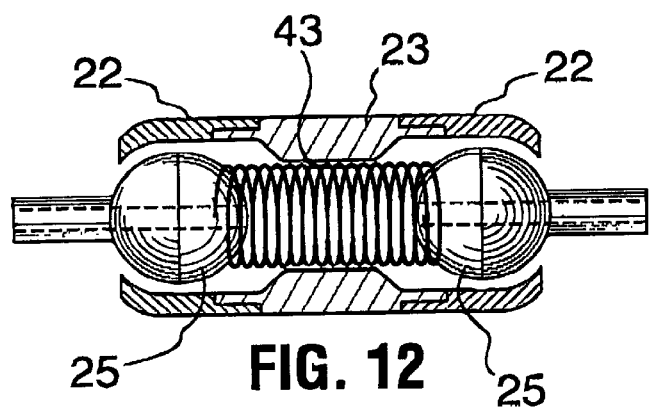
FIG. 12 illustrates a schematic section view of an embodiment of a universal joint construction with two balls, a tube and a helical spring.

It should be noted that the ball joint balls 25 can be pre-loaded against the ball joint sleeves 22 by internal springs 43, as shown in FIG. 12. This may allow the surgical arm 2 to hold its weight while the arm is not pressurized. Also note that another pressure level, rather than atmosphere, could be used to preload the arm brakes while it is in its limp or movable state. This pressure level could be used to adjust the arm stiffness while it is movable. Also, several levels of internal pressurization can be provided in order to control the arm stiffness.

Figure 13:
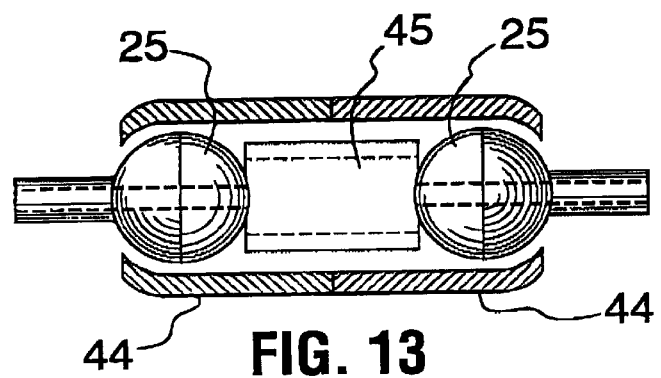
FIG. 13 illustrates a schematic section view of an embodiment of universal joint construction with two balls, and an outer tube and an inner tube.

It should also be understood that design modifications within the spirit of this invention can be made to make the arm construction simpler or cheaper. For example, FIG. 13 shows a link design that consists of only two sleeves 44 that attach to each other directly. An internal spacer 45 separates the ball joint balls 25 at the end of the links. The internal spacer 45 could be replaced, as mentioned above, with a spring (not shown).

Figure 14:
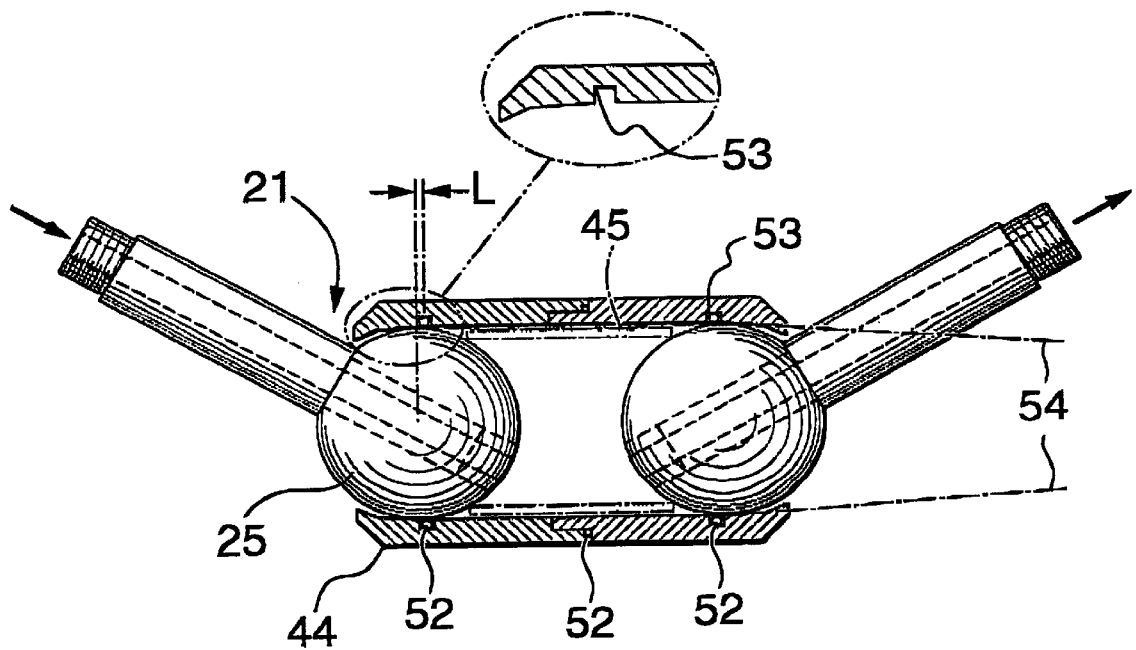
FIG. 14 illustrates a detailed section view of a further embodiment of joint construction which has enhanced holding force.

FIG. 14 illustrates a detail section view of a joint construction that allows for substantially greater holding force to be possible at each of the arm ball-joints 21. FIG. 14 illustrates another embodiment of sealing between ball-joint balls 25 and link sleeves 44. The link design in FIG. 14 also consists of two sleeves 44 that attach to each other directly. This embodiment uses steel (or other hard material) ball-joint balls with O-ring seals 52 located in place by O-ring grooves 53 in the surgical arm link sleeves 44. When the device is not pressurized, the ball-joint balls 25 are held lightly in a socket formed by the conical taper 54 and the O-rings 52. The O-rings 52 are placed a small distance L behind the ball centers. When the surgical arm is pressurized, the O-rings 52 are pushed against the ball-joint balls 25 and the O-ring grooves 53 and seal the interior of the link. An internal spacer 45 could be used optionally to ensure that the balls 25 are never unseated from the socket and pushed past the O-ring 52. The internal spacer 45 can be spring loaded.

In order to improve the arm holding force, the link sleeves 44 can be designed to have a conical taper 54 that increases the force between the ball-joint balls 25 and the link sleeves 44 by a wedge action. For taper 54 angles between 1 degree and 5 degrees, one can expect force amplifications approximately between 60 and 10. The taper angle should be selected to be small enough for the wedge action to provide adequate hold without damaging the ball-joint ball 25 or the link sleeves 44.

Both vacuum flow and pressurized gas flow for the tissue holder 1 and surgical arm 2 are controlled through use of valves in air flow channel 26, as shown in FIG. 1. These valves 26 could be located in a box on the floor or on a nearby table, but in a preferred solution, they could be mounted unobtrusively to a rail 29 on the side of the operating room table 46 with a clamp 47. The surgeon would control the vacuum and pressure flow through the valves 26 through use of a switch (not shown). For example for ease of application, this could be done through the use of a foot pedal.

The heart stabilizer presented above functions as follows. With the surgical arm pressure OFF, and the vacuum supply line 10 to the tissue holder also OFF, the surgical arm 2 is limp and the surgeon can position the tissue holder 1 onto the desired operating site unimpeded. The vacuum into the tissue holder 1 can be switched ON when desired, thus locking the tissue holder 1 to the operating site. Then, the gas pressure in the surgical arm 2 can also be switched ON, instantly locking the surgical arm 2 in position and therefore locking the tissue holder 1 and the surgical site to the patient's retractor 19 (bed or surgical stand). Should repositioning be required, the surgical arm 2 gas supply can be switched OFF when desired for unimpeded positioning of the tissue holder 1. Said switching may be accomplished by using one or two foot pedals, one or two hand switches on or near the operating table or a combination of the two. If required, the switching of tissue holder 1 vacuum and surgical arm 2 pressure could be coupled so that a single switch or foot pedal switches vacuum and pressure ON or OFF at the same time.

Features and Advantages of the Invention

Stabilization by suturing has several disadvantages. It takes time to set up, it does damage to heart tissue and there is still significant heart motion left.

Relative to previous devices used for cardiac tissue stabilization (Cremer, 1997; Guidant, 1977; Borst, 1996), the system according to the invention provides improved stabilization, activation and deployment. The device includes a surgical arm which is useful in any task that requires a "third hand" that can be quickly positioned, locked and later released.

Unlike the systems presented in Cremer, 1997, or Guidant, 1997, the cardiac tissue holder described in this invention uses vacuum to perform tissue immobilization. The use of suction allows greater range of application, as the device of the invention is not restricted to heart locations that can only be pushed down upon. The device exerts smaller maximal forces on the heart, and therefore is less likely to cause arythmias.

Relative to the "Octopus" device (Medtronic, 1997), the vacuum suction of the device according to this invention is provided in a large continuous chamber instead of across discrete suction cups. This permits lower suction pressures to be used for the same holding forces. In addition, the inhalation of tissue in the vacuum channel of the hollow C-channel, when the vacuum is activated, temporarily closes the coronary artery underneath the channel, thereby preventing the flow of blood into the suturing field.

As in prior designs, the tissue stabilizer according to this invention is mechanically affixed by a mount to a stable platform such as the patient's retractor, the operating table or the operating room floor. Prior mechanical holding devices involve the tightening of a cable clamp (Guidant, 1997; Cremer, 1997) or securing a bulky, cumbersome, support arm in several places as involved in the Octopus device (Borst, 1996). The use of mechanical clamps requires the tightening of a cable that can snap and that takes time to properly lock in place. The use of the Octopus arm requires the sequential tightening of several locking links.

The use of other surgical stabilizer devices mentioned in the background art is also not appropriate for cardiac tissue stabilization, The pneumatic arms reported (Auchinleck et al., 1992; McEwen et al., 1993; McEwen et al., 1993; Andronic Devices, 1994) are bulky and of limited dexterity. This is due to their design for high load applications which require that the pneumatic brakes be implemented as large, single-degree-of-freedom brakes. The design of such arms does not scale down easily and it would be unrealistic to imagine a twelve or eighteen-degree-of-freedom passive stabilizer, such as provided by the subject invention, made up of as many one-degree-of-freedom joints with pneumatic brakes between the links. The AESOP system (Sackier, 1996) teaches a motorized robot with angle sensors and motors at each axis. Such a system would be expensive, obtrusive and of marginal dexterity in an application that requires the arm to enter the thoracic cavity.

Although the piezoelectric brake arm presented in Erbse et al., 1997 could be miniaturized as a holder for application with a cardiac tissue stabilizer, the use of PZT material implies high voltages, proper insulation and electrical connectors, and would be difficult to sterilize, expensive, and risky to use in surgery.

The combination of a vacuum tissue holder and a pressurized surgical arm according to the subject invention for cardiac tissue stabilization is much easier to use and much less cumbersome than any prior art cardiac tissue stabilizing device. In particular, both tissue stabilization by the vacuum tissue holder and arm fixation to a reference frame are almost instantaneous and literally involve the flick of a switch or the push of a pedal. Solutions proposed in the prior art are time consuming since they involve the tightening of a cable clamp or securing a bulky, cumbersome support arm in several places.

The surgical arm of the subject invention is unobtrusive. It has been designed after conducting careful measurements of heart forces in animals and scaling to humans (Gilhuly, 1998). It can be sized properly and designed with multi-degree-of-freedom brakes, thereby saving space and expense. It is of very small size, having a maximum diameter of less than 3.5 cm. This provides minimal interference with the surgeons manipulating their surgical instruments to suture and allows secure mounting of the arm to the patient's retractor to couple its motion to the patient. Chest retractor mounting has several advantages. The arm does not interfere with the movement or work of the surgeons, as is the case with operating table or floor mounted arms. The surgical arm according to the invention can be smaller and lighter if mounted close to the heart, and patient motion, such as caused by coughing, has a reduced potential for patient injury due to collision with or pulling on the cardiac tissue.

The surgical arm according to the invention has many degrees of freedom, thereby giving it a highly dexterous workspace and allowing the surgeon to "route" the surgical arm so as to have little interference with the surgical field, the surgeons' hands and their instruments.

To summarize, with respect to prior art cardiac stabilizer designs, the cardiac tissue stabilizer and surgical arm of the subject invention has the following novel features:

(1) application of vacuum for tissue immobilization in a single large continuous chamber, thereby leading to strong stabilizing forces at low vacuum pressures and also leading to a bloodless operating field;

(2) easy set-up and nearly instantaneous locking and release;

(3) small size and lightweight, thereby making it non-obtrusive and mountable on the patient's retractor;

(4) safety and easy sterilization; and (5) high dexterity.

The improvements provided by this invention can be applied to a large set of problems encountered in surgery (e.g. tool positioning, tissue retraction and immobilization) and general mechanical repair (e.g. whenever something relatively small and light would be required to be held).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Kirkland, John W., et al. *Cardiac Surgery: Morphology, Diagnostic Criteria, Natural History, Techniques, Results and Indications*. Churchill-Livingstone Press, New York, 1993.
2. The Committee on Trauma, Division of Medical Sciences National Academy of Sciences. *Mechanical Devices to Assist the Failing Heart*. National Research Council, Washington, D.C., 1966.
3. Guidant Corporation, internet web page as of May, 1998, copyright 1997: *http://www.guidant.com/cvs/product/*.
4. Cremer, Jochen et al. "Off-Bypass Coronary Bypass Grafting via Minithoracotomy Using Mechanical Epicardial Stabilization". *Annals of Thoracic Surgery*, vol. 63, pp. S79–83, 1997.
5. Boonstra, Piet W., et al. "Local Immobilization of the Left Anterior Descending Artery for Minimally Invasive Coronary Bypass Grafting". *Annals of Thoracic Surgery*, vol. 63, pp. S76–78, 1997.
6. Borst, Cornelius, et al. "Coronary Artery Bypass Grafting without Cardio-Pulmonary Bypass and without Interruption of Native Coronary Flow Using Novel Anastomosis Site Restraining Device ('Octopus')". *Journal of American College of Cardiology*, vol. 27, no. 6, May 1996.
7. Medtronic Inc., internet web page as of May 1998, copyright 1997: *http://www.medtronic.com/mics/*.
8. Andronic Devices Inc., product literature, 1994.
9. Sackier, Jonathan M., and Wang, Yulun. "Robotically Assisted Laparoscopic Surgery: From Concept to Development". Computer Integrated Surgery, edited by R. H. Taylor, S. Lavallee, G. C. Burdea and R. Mosges, MIT Press, 1996.
10. Gilhuly, Terence. "Optical and physical heart stabilization for cardiac surgery". M.A.Sc. Thesis submitted The University of British Columbia, Vancouver, Canada, submitted confidentially Apr. 30, 1998, to appear June 1998.
11. Auchinleck et al. "Apparatus for Patient Limb Positioning". U.S. Pat. No. 5,104,103, Apr. 14, 1992.
12. McEwen et al. "Advanced Surgical Retractor". U.S. Pat. No. 5,201,325, Apr. 13, 1993.
13. McEwen et al. "Powered Surgical Retractor". U.S. Pat. No. 5,271,384, Dec. 21, 1993.
14. Computer Motion, internet web page, as of May 1998: *http://www.ComputerMotion.com*.
15. Erbse, St., et al. "Development of an Automatic Surgical Holding Based on Ergonomic Analysis". CVRMed-MRCAS'97: *Computer Vision, Virtual Reality and Robotics in Medicine, and Medical Robotics and Computer Assisted Surgery* conference proceedings, 1997.
16. Snyder, W. S. *Report on the Task Group on Reference Man*, International Commission on Radiological Protection #23, Pergamon Press, Oxford, U.K., 1975.

What is claimed is:

1. A surgical arm comprising:
   (a) a first hollow link;
   (b) a second hollow link;
   (c) a hollow universal joint connecting an end of the first Link with an end of the second link;
   (d) a support mount for the first link, the universal joint and the second link; and
   (d) a hollow tissue stabilizer connected to an end of a hollow link opposite to the hollow link that is proximate the support mount said hollow tissue stabilizer being constructed in the form of a hollow "C" with a cross-section wherein the top and two side walls of the cross-section are solid and the bottom side of the cross-section is open and unobstructed throughout its length, the internal radius of the "C" being within a range of about 7 to 14 nm, and an inner wall height of the "C" being within a range of between 4 and 8 mm.

2. A surgical arm as claimed in claim 1 including a third hollow link, and a second hollow universal joint, located between the first hollow link, first hollow universal joint and second hollow link, to form three links in series, connected by hollow universal joints between the respective links.

3. A surgical arm as claimed in claim 1 wherein the support mount is a clamp which can be detachably affixed to a stable body.

4. A surgical arm as claimed in claim 1 wherein an end of the first hollow link, remote from the first hollow universal joint is connected to the support mount by a hollow universal joint.

5. A surgical arm as claimed in claim 1 wherein an end of the second hollow link, remote from the hollow universal joint, is connected to the tissue stabilizer by a universal joint.

6. A surgical arm as claimed in claim 1 wherein the hollow universal joint is biased to hold a position when the first hollow link is moved relative to the second hollow link.

7. A surgical arm as claimed in claim 1 wherein the hollow universal joint comprises a first ball and a second ball connected together by a sleeve.

8. A surgical arm as claimed in claim 7 wherein one part of the first and second balls is constructed of metal and a second part of the first and second balls is constructed of a resilient material.

9. A surgical arm as claimed in claim 7 wherein the first ball and the second ball are biased by a metal spring.

10. A surgical arm as claimed in claim 8 wherein the first ball and the second ball are biased by a spacer.

11. A surgical arm as claimed in claim 7 wherein the first ball and the second ball which are housed in a tubular sleeve, each internal end of the tubular sleeve having a conical taper of an angle between 1 and 5 degrees which first and second ball exert a force on the interior of the tubular sleeve when air pressure is applied to the interior of the tubular sleeve.

12. A surgical arm as claimed in claim 1 wherein the hollow "C"-shaped tissue stabilizer has openings therein which permit the tissue stabilizer to affix to tissue when a vacuum is applied to the interior of the "C"-shaped hollow tissue stabilizer.

13. A surgical arm as claimed in claim 1 including a suction machine which draws a vacuum on the interior of the surgical arm and tissue stabilizer.

14. A surgical arm as claimed in claim 7 including a groove in the sleeve and an O-ring in the groove.

15. A surgical arm as claimed in claim 1 wherein the first hollow link, the second hollow link and the hollow universal joint are pressurized and the hollow tissue stabilizer has a vacuum drawn on it.

16. A tissue stabilizer for releasable vacuum attachment to living tissue, said tissue stabilizer being constructed in the form of a hollow "C" with a cross-section wherein the top and two side walls of the cross-section are solid and the bottom side of the cross-section is open and unobstructed throughout its length, the internal radius of the "C" being within a range of about 7 to 14 mm, and an inner wall height of the "C" being within a range of between 4 and 8 mm.

17. A tissue stabilizer as claimed in claim 16 wherein the tissue stabilizer is adapted to be releasably vacuum attached to a living human hart.

18. A tissue stabilizer as claimed in claim 17 wherein the vacuum pressure is controlled by a computer.

* * * * *